(12) United States Patent
Zhang et al.

(10) Patent No.: US 9,927,348 B2
(45) Date of Patent: Mar. 27, 2018

(54) INDIRECTLY DETERMINING EXHAUST GAS PARAMETERS

(71) Applicant: General Electric Company, Schenectady, NY (US)

(72) Inventors: Daili Zhang, Humble, TX (US); Constantin Dinu, Greer, SC (US)

(73) Assignee: General Electric Company, Schenectady, NY (US)

( * ) Notice: Subject to any disclaimer, the term of this patent is extended or adjusted under 35 U.S.C. 154(b) by 301 days.

(21) Appl. No.: 14/948,750

(22) Filed: Nov. 23, 2015

(65) Prior Publication Data
US 2017/0145924 A1    May 25, 2017

(51) Int. Cl.
| | |
|---|---|
| *F02C 9/16* | (2006.01) |
| *G01N 19/10* | (2006.01) |
| *G01M 15/14* | (2006.01) |
| *G01M 15/10* | (2006.01) |
| *G01K 13/02* | (2006.01) |
| *G01F 1/00* | (2006.01) |
| *F02C 9/26* | (2006.01) |
| *F02C 9/28* | (2006.01) |

(52) U.S. Cl.
CPC .............. *G01N 19/10* (2013.01); *F02C 9/26* (2013.01); *F02C 9/28* (2013.01); *G01F 1/00* (2013.01); *G01K 13/02* (2013.01); *G01M 15/10* (2013.01); *G01M 15/104* (2013.01); *G01M 15/14* (2013.01); *F05D 2270/0831* (2013.01); *F05D 2270/301* (2013.01); *F05D 2270/303* (2013.01); *F05D 2270/3061* (2013.01); *F05D 2270/311* (2013.01); *F05D 2270/312* (2013.01); *F05D 2270/313* (2013.01); *G01K 2013/024* (2013.01)

(58) Field of Classification Search
CPC .............. F02D 41/1446–41/1494; G01N 19/10
USPC .................................. 702/104, 127; 123/676
See application file for complete search history.

(56) References Cited

U.S. PATENT DOCUMENTS

| | | | |
|---|---|---|---|
| 5,219,228 A | 6/1993 | Ker et al. | |
| 6,679,238 B2 * | 1/2004 | Nebiyeloul-Kifle | F02D 41/1494 123/676 |
| 8,019,563 B2 * | 9/2011 | Moser | F02D 41/1446 702/104 |

* cited by examiner

*Primary Examiner* — Bo Fan
(74) *Attorney, Agent, or Firm* — Ernest G. Cusick; Hoffman Warnick LLC

(57) ABSTRACT

Various embodiments include a system having: a computing device configured to monitor a gas turbine (GT) by: determining a moisture content and/or an oxygen content of inlet air entering the inlet of the GT compressor section; determining a corresponding one of the moisture content and/or the oxygen content of exhaust gas from the GT turbine section; calculating a flow rate of the exhaust gas from the turbine section and a flow rate of the inlet air entering the inlet of the compressor section based upon the moisture content and/or the oxygen content of the inlet air and the exhaust gas; and calculating a temperature of the exhaust gas and an energy of the exhaust gas from the turbine section based upon the flow rate of the exhaust gas from the turbine and the flow rate of the inlet air entering the inlet of the compressor section.

20 Claims, 4 Drawing Sheets

INDIRECTLY DETERMINING EXHAUST GAS PARAMETERS

FIELD OF THE INVENTION

The subject matter disclosed herein relates to turbomachines (e.g., turbines). More particularly, the subject matter disclosed herein relates to determining exhaust gas parameters in turbines, such as gas turbines, for the purposes of analyzing, monitoring and/or controlling those turbines along with related downstream equipment.

BACKGROUND OF THE INVENTION

Gas turbomachines, also referred to as gas turbines, are typically designed, constructed and tested according to particular performance standards, so that each gas turbine can meet the desired operating parameters desired by its user (e.g., a customer). Many gas turbines are sold to customers with certain associated performance guarantees, which are verified by conducting rigorous performance tests. The subject gas turbine is equipped with precision instrumentation which shall meet the accuracy requirements imposed by the testing code or agreed upon by all parties. A data acquisition system is conventionally installed to collect data relevant to the guarantee. Installing required instrumentation, setting up the test environment, collecting performance and other data, and processing the data requires significant resources in terms of time and costs. As such, many end users either forego this invasive performance testing, or opt for more crude measurements of performance, which are prone to error. In either case, the end user does not obtain an accurate understanding of the performance of the gas turbine.

In order to monitor gas turbine and related downstream equipment while that equipment is online, multiple thermocouple systems are conventionally installed. This equipment can be costly to procure and install, and the process of effectively installing these systems is complex.

BRIEF DESCRIPTION OF THE INVENTION

Various embodiments of the disclosure include a system having: at least one computing device configured to a gas turbine (GT) having a compressor section with an inlet, a combustor section fluidly connected with the compressor section, and a turbine section fluidly connected with the combustor section, by performing actions including: determining at least one of a moisture content or an oxygen content of inlet air entering the inlet of the compressor section; determining a corresponding one of the at least one of the moisture content or the oxygen content of exhaust gas from the turbine section; calculating a flow rate of the exhaust gas from the turbine section and a flow rate of the inlet air entering the inlet of the compressor section based upon the at least one of the moisture content or the oxygen content of the inlet air and the exhaust gas; and calculating a temperature of the exhaust gas and an energy of the exhaust gas from the turbine section based upon the flow rate of the exhaust gas from the turbine and the flow rate of the inlet air entering the inlet of the compressor section.

A first aspect of the disclosure includes a system having: at least one computing device configured to monitor a gas turbine (GT) having a compressor section with an inlet, a combustor section fluidly connected with the compressor section, and a turbine section fluidly connected with the combustor section, by performing actions including: determining at least one of a moisture content or an oxygen content of inlet air entering the inlet of the compressor section; determining a corresponding one of the at least one of the moisture content or the oxygen content of exhaust gas from the turbine section; calculating a flow rate of the exhaust gas from the turbine section and a flow rate of the inlet air entering the inlet of the compressor section based upon the at least one of the moisture content or the oxygen content of the inlet air and the exhaust gas; and calculating a temperature of the exhaust gas and an energy of the exhaust gas from the turbine section based upon the flow rate of the exhaust gas from the turbine and the flow rate of the inlet air entering the inlet of the compressor section.

A second aspect of the disclosure includes a computer program product having program code, which when executed by at least one computing device, causes the at least one computing device to monitor a gas turbine (GT) having a compressor section with an inlet, a combustor section fluidly connected with the compressor section, and a turbine section fluidly connected with the combustor section, by performing actions including: calculating a flow rate of the exhaust gas from the turbine section and a flow rate of the inlet air entering the inlet of the compressor section based upon the at least one of the moisture content or the oxygen content of the inlet air and the exhaust gas; and calculating a temperature of the exhaust gas and an energy of the exhaust gas from the turbine section based upon the flow rate of the exhaust gas from the turbine and the flow rate of the inlet air entering the inlet of the compressor section.

A third aspect of the disclosure includes a system having: a gas turbine (GT) including a compressor section with an inlet, a combustor section fluidly connected with the compressor section, and a turbine section fluidly connected with the combustor section; and the at least one computing device configured to perform actions including: determining at least one of a moisture content or an oxygen content of inlet air entering the inlet of the compressor section; determining a corresponding one of the at least one of the moisture content or the oxygen content of exhaust gas from the turbine section; calculating a flow rate of the exhaust gas from the turbine section and a flow rate of the inlet air entering the inlet of the compressor section based upon the at least one of the moisture content or the oxygen content of the inlet air and the exhaust gas; and calculating a temperature of the exhaust gas and an energy of the exhaust gas from the turbine section based upon the flow rate of the exhaust gas from the turbine and the flow rate of the inlet air entering the inlet of the compressor section.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

Figure 1:
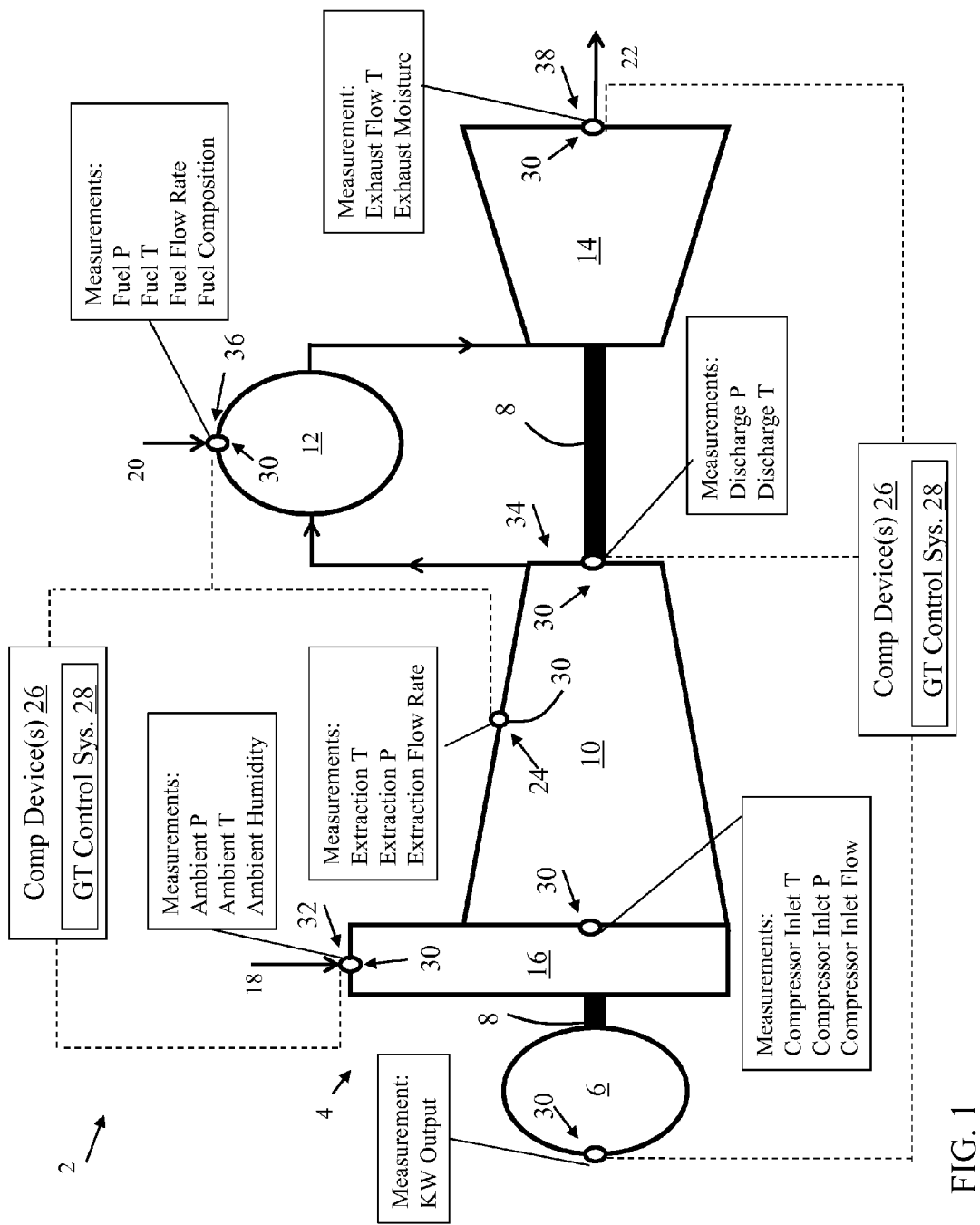
FIG. 1 shows a schematic depiction of a system including a gas turbine (GT) system, according to various embodiments of the disclosure.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the subject matter disclosed herein relates to turbomachines (e.g., turbines). More particularly, the subject matter disclosed herein relates to determining exhaust gas parameters in turbines, such as gas turbines, for monitoring (as used herein to refer to analyzing, monitoring and/or controlling) those turbines as well as downstream components.

In contrast to conventional approaches, various aspects of the disclosure include systems, computer program products and associated methods to determine exhaust parameters (e.g., exhaust gas temperature, exhaust gas energy, exhaust gas flow rate, etc.) of a gas turbine (GT) without requiring that the GT be equipped with multiple thermo-couples in the exhaust system. This approach can utilize measurement hardware already in place for detecting compliance with emissions standards (e.g., oxygen in GT exhaust), and for GT existed control system. The systems, computer program products and associated methods can calculate exhaust parameters of the GT using heat-balance and mass-balance equations, based upon a known humidity or oxygen level of the inlet air and the exhaust gas.

In the following description, reference is made to the accompanying drawings that form a part thereof, and in which is shown by way of illustration specific example embodiments in which the present teachings may be practiced. These embodiments are described in sufficient detail to enable those skilled in the art to practice the present teachings and it is to be understood that other embodiments may be utilized and that changes may be made without departing from the scope of the present teachings.

FIG. 1 shows a schematic depiction of a system 2 according to various embodiments of the disclosure. As shown, system 2 can include a gas turbomachine (e.g., a gas turbine) 4 connected with a load device 6 (e.g., a dynamoelectric machine such as a generator), e.g., via a shaft 8, as is known in the art. Gas turbomachine (GT) 4 can include a compressor section 10, a combustor section 12 fluidly coupled with the compressor section 10, and a turbine section 14 fluidly coupled with the combustor section 12 and mechanically coupled with compressor section 10 via shaft 8 (which may be same as other shaft 8, or a separate shaft). Compressor section 10 includes an inlet filter 16 which filters inlet air 18 (e.g., ambient air) prior to entering the body of compressor section 10. Fuel 20 is injected into combustor section 12, and combined with compressed air from compressor section 10 in order to create a working fluid (hot gas) that is subsequently fed to turbine section 14 to drive rotor blades and cause rotation of shaft 8. Exhaust gas 22 is emitted from turbine section 14 after performing mechanical work on the rotor blades, as is known in the art. As shown, compressor section 12 can further include an extraction location 24, where a portion of the compressed air flow is extracted and provided to another location in a turbine system (e.g., turbine cooling path).

As shown in FIG. 1, system 2 can include at least one computing device 26 configured to analyze GT 4 and related downstream equipment. Computing device(s) 26 can be hard-wired and/or wirelessly connected to GT 4 (and related downstream equipment) via any conventional means. In various embodiments, computing device(s) 26 can include a control system, as described herein, for analyzing operations of GT 4 (and related downstream equipment). According to various embodiments, computing device(s) 26 can include a GT control system 28, described with respect to various embodiments herein. GT control system 28 can control a gas turbine (e.g., GT 4) using various processes described herein.

System 2 can further include a plurality of sensors 30 at distinct locations on GT 4, for measuring various parameters of GT 4. In particular, sensors 30 can be located proximate inlet 32 of compressor section 10, proximate inlet filter 16 (downstream of inlet filter 16, in compressor section 10), at outlet 34 of compressor section 10, at inlet 36 of combustor section 12 (e.g., for monitoring fuel flow to combustor section 12), and at outlet 38 of turbine section 14 (for monitoring exhaust gas flow from turbine section 14). Sensors 30 may also be used to measure the output (e.g., kilo-watt, kW output) of load device 6. At distinct locations, a variety of sensors 30 can be utilized to measure qualities such as temperature (e.g., via temperature sensors), pressure (e.g., via pressure sensors), fluid flow/flow rate (e.g., via flow meters), humidity (e.g., via humidity sensors), fuel consumption (e.g., via consumption sensors, known in the art), moisture content (e.g., via moisture sensors, if utilized), oxygen content (e.g., via oxygen sensors, if utilized), and/or output (e.g., via electricity meters).

Figure 2:
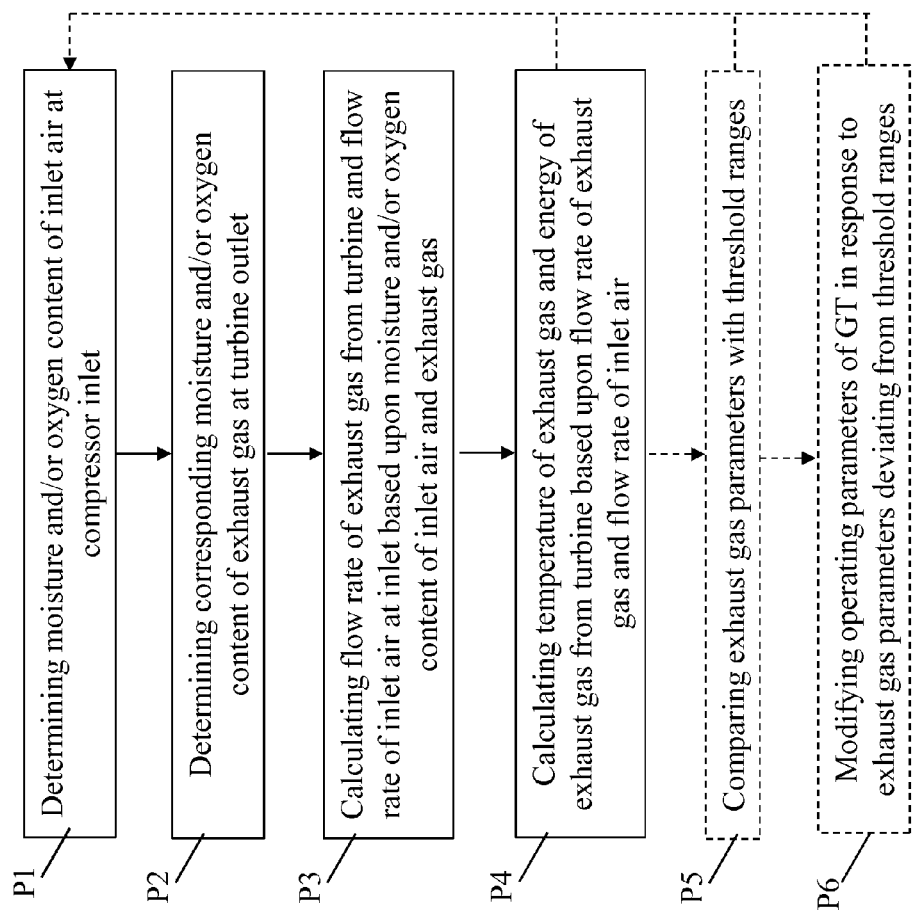
FIG. 2 shows a flow diagram illustrating a method performed according to particular embodiments of the disclosure.

FIG. 2 shows a flow diagram illustrating a process of monitoring and/or controlling a GT 4 (and related downstream equipment) according to various embodiments of the invention. These processes can be performed, e.g., by at least one computing device 26 including GT control system 28, as described herein. In other cases, these processes can be performed according to a computer-implemented method of controlling GT 4. In still other embodiments, these processes can be performed by executing computer program code, causing computing device(s) 26 to control operation of GT 4. In general, the process can include the following sub-processes:

Process P1: determining at least one of a moisture content or an oxygen content of inlet air entering inlet 32 of compressor section 10. This process can include measuring the moisture content and/or the oxygen content of inlet air entering inlet 32 of compressor section 10 using one or more sensors 30.

Process P2: determining a corresponding one of the moisture content and/or oxygen content of exhaust gas from outlet 38 of turbine section 14. In various embodiments, this process can include measuring the moisture content and/or the oxygen content of exhaust gas exiting outlet 38 of turbine section 14 using one or more of sensors 30. In some embodiments, both the moisture content and the oxygen content of the inlet air (at inlet 32) and the exhaust gas (at outlet 38) are measured using sensors 30. It is understood that the moisture content and the oxygen content are independent variables, and as such, measuring both moisture content and oxygen content can provide a more accurate composite measurement of the characteristics of the GT 4.

Process P3: calculating a flow rate of the exhaust gas from turbine section 14 (at outlet 38) and a flow rate of the inlet air entering inlet 32 of compressor section 10 based upon the at least one of the moisture content or the oxygen content of the inlet air and the exhaust gas (via sensors 30).

Process P4: calculating a temperature of the exhaust gas and an energy of the exhaust gas from turbine section 14 (at outlet 38) based upon the flow rate of the exhaust gas from the turbine section 14 and the flow rate of the inlet air entering inlet 32 of compressor section 10. This process can include calculating temperature and energy using mass conservation and energy conservation equations including:

$$\Sigma_i^n w_{in\_i} = \Sigma_j^m w_{out\_j} \quad \text{(Equation 1)}$$

Where:

$w_{in\_i}$: the ith incoming flow to the gas turbine section 14 across its boundary;

$w_{out\_j}$: the jth outgoing flow from the gas turbine section 14 across its boundary; and:

$$\Sigma_i^k E_{in\_i} = \Sigma_j^i E_{out\_j} \quad \text{(Equation 2)}$$

Where, $E_{in\_i}$: the ith incoming energy to the gas turbine section 14 across its boundary; and $E_{out\_j}$: the jth outgoing energy from the gas turbine section 14 across its boundary.

As is well known in the art exhaust gas temperature can be derived from the calculated exhaust gas energy, using conventional conversion equations which account for particular characteristics of the fluid (e.g., gas) and/or conversion tables. That is, exhaust gas temperature is a function of exhaust energy, and as such, can be derived after solving the energy/mass conservation equations noted herein for the particular fluid (e.g., gas).

Process P1-P4 are shown schematically in FIG. 2. In some particular embodiments (optionally, as depicted in phantom), the process can further include:

Process P5: comparing the parameters of the exhaust gas (from outlet 38) with threshold ranges of exhaust gas parameter values. The threshold ranges can be based upon a data model of desirable exhaust gas parameters, and can span between +/− values surrounding desirable exhaust gas parameters. For example, a threshold range for exhaust energy can span between approximately +/−0.5 to approximately +/−1 percent deviation from a target (e.g., design) exhaust energy value. Further, a threshold range for exhaust temperature can span between approximately +/−5 degrees Celsius to approximately +/−10 degrees Celsius. The model can be constructed, derived, calculated, etc. from design operating conditions of GT 4 (and related downstream equipment), for example, based upon exhaust gas conditions at design load. The model may be pre-constructed, and stored in a memory sector of computing device(s) 26.

Process P6: modifying an operating parameter of GT 4 (and related downstream equipment) in response to the parameters of the exhaust gas deviating from the threshold ranges (e.g., falling outside of the threshold ranges). In some cases, modifying the operating parameter(s) of GT 4 (and related downstream equipment) includes modifying a firing temperature of combustor section 12 (e.g., increasing a firing temperature where exhaust gas energy/flow/temperature is below threshold range, or decreasing the firing temperature where exhaust gas energy/flow/temperature is above threshold ranges).

It is understood that processes P1-P6 (or P1-P4, where P5 and/or P6 are not performed), can be iterated on a periodic, or constant basis. Further, processes P1-6 can be performed in response to particular operating conditions of GT 4 (and related downstream equipment), for example, when a startup operation is initiated (e.g., control instructions for startup are obtained), or when a ramp-up is initiated (e.g., control instructions for increased output are obtained). Additionally, these processes can be repeated according to any schedule to control operation of GT 4 (and related downstream equipment) as described herein.

It is understood that in the flow diagrams shown and described herein, other processes may be performed while not being shown, and the order of processes can be rearranged according to various embodiments. Additionally, intermediate processes may be performed between one or more described processes. The flow of processes shown and described herein is not to be construed as limiting of the various embodiments.

Figure 3:
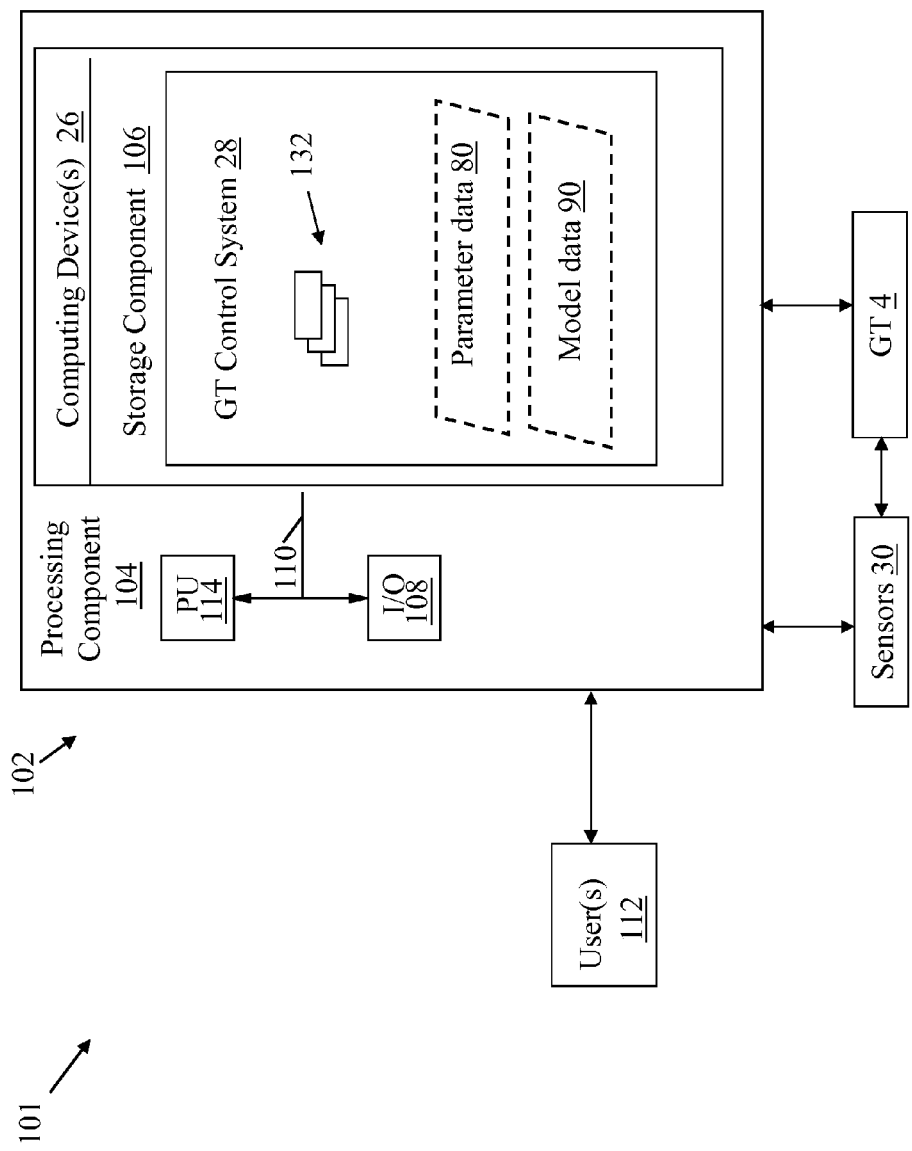
FIG. 3 shows an environment including a system for controlling the GT of FIG. 1, according to various embodiments of the disclosure.

FIG. 3 shows an illustrative environment 101 including a GT control system 28, for performing the functions described herein according to various embodiments of the invention. To this extent, the environment 101 includes a computer system 102 that can perform one or more processes described herein in order to monitor and/or control GT 4 (FIG. 1). In particular, the computer system 102 is shown as including the GT control system 28, which makes computer system 102 operable to control/monitor operation of a GT 4 by performing any/all of the processes described herein and implementing any/all of the embodiments described herein.

The computer system 102 is shown including a computing device 26, which can include a processing component 104 (e.g., one or more processors), a storage component 106 (e.g., a storage hierarchy), an input/output (I/O) component 108 (e.g., one or more I/O interfaces and/or devices), and a communications pathway 110. In general, the processing component 104 executes program code, such as the GT control system 28, which is at least partially fixed in the storage component 106. While executing program code, the processing component 104 can process data, which can result in reading and/or writing transformed data from/to the storage component 106 and/or the I/O component 108 for further processing. The pathway 110 provides a communications link between each of the components in the computer system 102. The I/O component 108 can comprise one or more human I/O devices, which enable a user (e.g., a human and/or computerized user) 112 to interact with the computer system 102 and/or one or more communications devices to enable the system user 112 to communicate with the computer system 102 using any type of communications link. To this extent, the GT control system 28 can manage a set of interfaces (e.g., graphical user interface(s), application program interface, etc.) that enable human and/or system users 112 to interact with the GT control system 28. Further, the GT control system 28 can manage (e.g., store, retrieve, create, manipulate, organize, present, etc.) data, such as parameter data 80 (e.g., data about temperature(s), pressure(s), flow rate(s), humidity, fuel composition, moisture content, kW output, etc. as indicated (e.g., measured) by sensors 30) and/or model data 90 (e.g., including threshold data derived from models of GT 4, with data such as enthalpy, pressure, temperature, flow requirements, output, etc.) using any solution, e.g., via wireless and/or hardwired means.

In any event, the computer system 102 can comprise one or more general purpose computing articles of manufacture (e.g., computing devices) capable of executing program code, such as the GT control system 28, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the GT control system 28 can be embodied as any combination of system software and/or application software. It is further understood that the GT control system 28 can be implemented in a cloud-based computing environment, where one or more processes are performed at distinct computing devices (e.g., a plurality of computing devices 26), where one or more of those distinct computing devices may contain only some of the components shown and described with respect to the computing device 26 of FIG. 4.

Further, the GT control system 28 can be implemented using a set of modules 132. In this case, a module 132 can enable the computer system 102 to perform a set of tasks used by the GT control system 28, and can be separately developed and/or implemented apart from other portions of the GT control system 28. As used herein, the term "component" means any configuration of hardware, with or without software, which implements the functionality described in conjunction therewith using any solution, while the term "module" means program code that enables the computer system 102 to implement the functionality described in conjunction therewith using any solution. When fixed in a storage component 106 of a computer system 102 that includes a processing component 104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 102.

When the computer system 102 comprises multiple computing devices, each computing device may have only a portion of GT control system 28 fixed thereon (e.g., one or more modules 132). However, it is understood that the computer system 102 and GT control system 28 are only representative of various possible equivalent computer systems that may perform a process described herein. To this extent, in other embodiments, the functionality provided by the computer system 102 and GT control system 28 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 102 includes multiple computing devices 26, the computing devices can communicate over any type of communications link. Further, while performing a process described herein, the computer system 102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

While shown and described herein as a method and system for controlling operation of a GT 4 (and related downstream equipment) (FIG. 1), it is understood that aspects of the invention further provide various alternative embodiments. For example, in one embodiment, the invention provides a computer program fixed in at least one computer-readable medium, which when executed, enables a computer system to control/monitor operation of GT 4. To this extent, the computer-readable medium includes program code, such as the GT control system 28 (FIG. 3), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the GT control system 28 (FIG. 3), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of controlling operation of a GT 4 (FIG. 1). In this case, a computer system, such as the computer system 102 (FIG. 3), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the various embodiments of the invention, including, e.g., the GT control system 28, is to analyze operation of a GT. It is understood that according to various embodiments, the GT control system 28 could be implemented to control operation of a plurality of GTs, such as GT 4 described herein.

Figure 4:
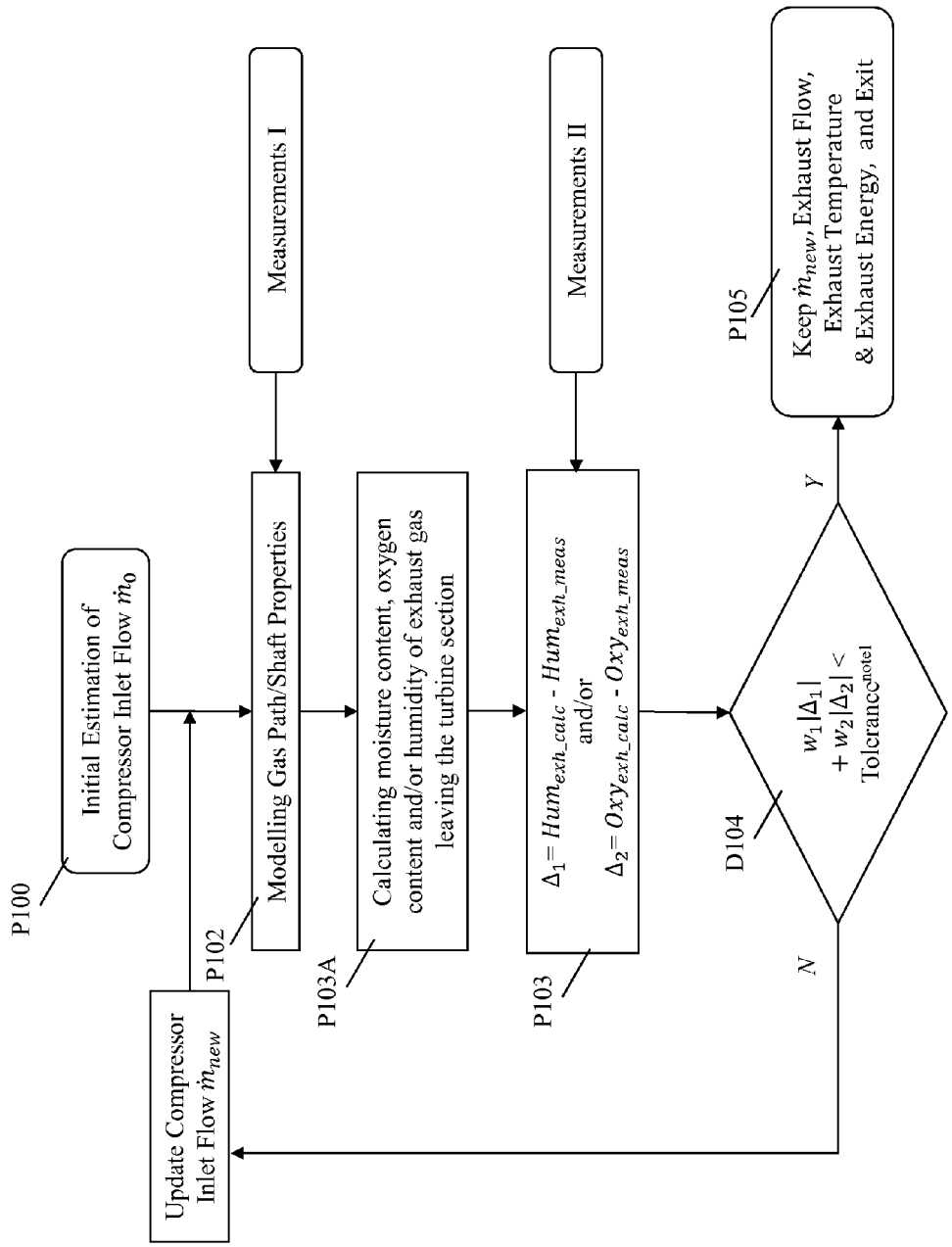
FIG. 4 shows a flow diagram illustrating an example method performed according to various particular embodiments of the disclosure.

FIG. 4 is a flow diagram illustrating an example process flow according to various particular embodiments, which includes the following processes:

Process P100: estimating an initial airflow into the compressor 12, based upon known parameters of the system 2;

Process P102: modeling the gas path and shaft 8 properties of system 2, using inputs such as inlet air characteristics as well as outlet gas characteristics, in addition to shaft 8 properties. This calculation involves using various measured quantities (measurement(s) I), including: inlet air temperature and pressure at compressor 12; inlet humidity and/or oxygen level at compressor 12; discharge temperature and/or pressure at compressor 12; fuel flow rate(s), temperature(s), pressure(s) and compositions of fuel at areas in system 2; exhaust gas humidity and/or oxygen level; output from generator 6; and/or flow rate, temperature and/or pressure at extraction location 24;

Process P103A: calculating the moisture content, oxygen content and/or humidity of the exhaust gas leaving the turbine section 14, using the model in process P102;

Process P103: calculating the difference between the measured humidity of the exhaust gas leaving the turbine section 14 and the calculated humidity of that exhaust gas (P103A), and calculating the difference between the measured oxygen content in the exhaust gas leaving the turbine section 14 and the calculated oxygen content of that exhaust gas (P103A). This process includes using measured quantities (measurement(s) II) including measured exhaust gas moisture ($Hum_{exh\_meas}$) and/or measured oxygen content ($Oxy_{exh\_meas}$) in the exhaust gas;

Decision D104: is the sum of exhaust energy as a function of the difference between measured exhaust humidity and calculated exhaust energy, and exhaust energy as a function of the difference between measured exhaust oxygen content and calculated exhaust oxygen content below a tolerance? It is understood that if corresponding measurements (in terms of humidity or oxygen, as provided in Measurements II) are not available, the corresponding value of $w_1$ and/or $w_2$ is set to zero;

Process P105: If Yes in Decision D104, then maintain input exhaust flow, exhaust temperature and exhaust energy;

If No to Decision D104, process P106 includes updating the compressor inlet flow measurement and repeating the process flow beginning at process P102.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
    at least one computing device configured to monitor a gas turbine (GT) having a compressor section with an inlet, a combustor section fluidly connected with the compressor section, and a turbine section fluidly connected with the combustor section, by performing actions including:
        determining at least one of a moisture content or an oxygen content of inlet air entering the inlet of the compressor section;
        determining a corresponding one of the at least one of the moisture content or the oxygen content of exhaust gas from the turbine section;
        calculating a flow rate of the exhaust gas from the turbine section and a flow rate of the inlet air entering the inlet of the compressor section based upon the at least one of the moisture content or the oxygen content of the inlet air and the exhaust gas; and
        calculating a temperature of the exhaust gas and an energy of the exhaust gas from the turbine section based upon the flow rate of the exhaust gas from the turbine and the flow rate of the inlet air entering the inlet of the compressor section.

2. The system of claim 1, wherein the at least one computing device is further configured to compare the parameters (flow/energy/temperature) of the exhaust gas with a threshold range of exhaust gas parameter values.

3. The system of claim 2, wherein the at least one computing device is further configured to modify at least one operating parameter of the GT in response to the parameter values of the exhaust gas deviating from the threshold ranges.

4. The system of claim 3, wherein the modifying of the operating parameter of the GT includes modifying a firing temperature of the combustor section.

5. The system of claim 3, wherein the threshold ranges includes approximately a +/−0.5 percent deviation to approximately a +/−1 percent deviation from a design exhaust energy value, or approximately a +/−5 degree Celsius deviation to approximately a +/−20 degree Celsius deviation from a design exhaust temperature value.

6. The system of claim 1, wherein the determining of the at least one of the moisture content or the oxygen content of the inlet air and the determining of the corresponding one of the at least one of the moisture content or the oxygen content of exhaust gas from the turbine section includes measuring the at least one of the moisture content or the oxygen content of the inlet air and the corresponding one of the at least one of the moisture content or the oxygen content of exhaust gas from the turbine section using a set of sensors.

7. The system of claim 1, wherein both the moisture content and the oxygen content of the inlet air and the exhaust gas are determined, wherein the moisture content and the oxygen content are independent variables.

8. A computer program product comprising program code, which when executed by at least one computing device, causes the at least one computing device to monitor a gas turbine (GT) having a compressor section with an inlet, a combustor section fluidly connected with the compressor section, and a turbine section fluidly connected with the combustor section, by performing actions including:

determining at least one of a moisture content or an oxygen content of inlet air entering the inlet of the compressor section;

determining a corresponding one of the at least one of the moisture content or the oxygen content of exhaust gas from the turbine section;

calculating a flow rate of the exhaust gas from the turbine section and a flow rate of the inlet air entering the inlet of the compressor section based upon the at least one of the moisture content or the oxygen content of the inlet air and the exhaust gas; and calculating a temperature of the exhaust gas and an energy of the exhaust gas from the turbine section based upon the flow rate of the exhaust gas from the turbine and the flow rate of the inlet air entering the inlet of the compressor section.

9. The computer program product of claim 8, wherein the program code causes the at least one computing device to further compare the parameters (flow/energy/temperature) of the exhaust gas with threshold ranges of exhaust parameter values.

10. The computer program product of claim 9, wherein the program code causes the at least one computing device to further modify an operating parameter of the GT in response to the parameters of the exhaust gas deviating from the threshold ranges.

11. The computer program product of claim 10, wherein the modifying of the operating parameter of the GT includes modifying a firing temperature of the combustor section.

12. The computer program product of claim 10, wherein the threshold range includes approximately a +/−0.5 percent deviation to approximately a +/−1 percent deviation from a design exhaust energy value, or approximately a +/−5 degree Celsius deviation to approximately a +/−20 degree Celsius deviation from a design exhaust temperature value.

13. The computer program product of claim 8, wherein the determining of the at least one of the moisture content or the oxygen content of the inlet air and the determining of the corresponding one of the at least one of the moisture content or the oxygen content of exhaust gas from the turbine section includes measuring the at least one of the moisture content or the oxygen content of the inlet air and the corresponding one of the at least one of the moisture content or the oxygen content of exhaust gas from the turbine section using a set of sensors.

14. The computer program product of claim 8, wherein both the moisture content and the oxygen content of the inlet air and the exhaust gas are determined, wherein the moisture content and the oxygen content are independent variables.

15. A system comprising:

a gas turbine (GT) having a compressor section with an inlet, a combustor section fluidly connected with the compressor section, and a turbine section fluidly connected with the combustor section; and at least one computing device coupled with the GT, the at least one computing device configured to perform actions including:

determining at least one of a moisture content or an oxygen content of inlet air entering the inlet of the compressor section;

determining a corresponding one of the at least one of the moisture content or the oxygen content of exhaust gas from the turbine section;

calculating a flow rate of the exhaust gas from the turbine section and a flow rate of the inlet air entering the inlet of the compressor section based upon the at least one of the moisture content or the oxygen content of the inlet air and the exhaust gas; and calculating a temperature of the exhaust gas and an energy of the exhaust gas from the turbine section based upon the flow rate of the exhaust gas from the turbine and the flow rate of the inlet air entering the inlet of the compressor section.

16. The system of claim 15, wherein the at least one computing device is further configured to compare the energy of the exhaust gas with a threshold range of exhaust energy values.

17. The system of claim 16, wherein the at least one computing device is further configured to modify an operating parameter of the GT in response to the energy of the exhaust gas deviating from the threshold range.

18. The system of claim 17, wherein the modifying of the operating parameter of the GT includes modifying a firing temperature of the combustor section.

19. The system of claim 17, wherein the threshold range includes approximately a +/−0.5 percent deviation to approximately a +/−1 percent deviation from a design exhaust energy value, or approximately a +/−5 degree Celsius deviation to approximately a +/−20 degree Celsius deviation from a design exhaust temperature value.

20. The system of claim 15, wherein both the moisture content and the oxygen content of the inlet air and the exhaust gas are determined, wherein the moisture content and the oxygen content are independent variables.

\* \* \* \* \*